(12) United States Patent
Barker, Jr. et al.

(10) Patent No.: US 7,967,847 B2
(45) Date of Patent: Jun. 28, 2011

(54) SPINAL STABILIZATION AND RECONSTRUCTION WITH FUSION RODS

(75) Inventors: Boyd Thomas Barker, Jr., Bartlett, TN (US); Eric Steven Heinz, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 325 days.

(21) Appl. No.: 11/491,724

(22) Filed: Jul. 24, 2006

(65) Prior Publication Data
US 2008/0021461 A1  Jan. 24, 2008

(51) Int. Cl.
*A61B 17/70* (2006.01)
(52) U.S. Cl. .................................................. 606/261
(58) Field of Classification Search .............. 606/60, 606/246, 254–256, 259–261, 264, 265, 279
See application file for complete search history.

(56) References Cited

U.S. PATENT DOCUMENTS

| | | |
|---|---|---|
| 3,242,922 A | 3/1966 | Thomas |
| 4,773,402 A | 9/1988 | Asher et al. |
| 5,000,165 A | 3/1991 | Watanabe |
| 5,306,275 A | 4/1994 | Bryan |
| 5,593,407 A | 1/1997 | Reis |
| 5,609,637 A | 3/1997 | Biedermann et al. |
| 5,897,556 A | 4/1999 | Drewry et al. |
| 6,086,613 A | 7/2000 | Camino et al. |
| 6,290,703 B1 | 9/2001 | Ganem |
| 6,520,990 B1 | 2/2003 | Ray |
| 7,060,073 B2 * | 6/2006 | Frey et al. ................... 606/85 |
| 2004/0153070 A1 * | 8/2004 | Barker et al. .............. 606/61 |
| 2006/0052785 A1 | 3/2006 | Augostino et al. |
| 2006/0058791 A1 * | 3/2006 | Broman et al. ............ 606/61 |
| 2009/0036985 A1 * | 2/2009 | Whiting .................. 623/17.11 |

* cited by examiner

*Primary Examiner* — Eduardo C Robert
*Assistant Examiner* — Sameh Boles (57) ABSTRACT

Spinal fusion rods extend along a longitudinal axis and include a rod portion and a fusion portion along the longitudinal axis. The fusion rods can be employed alone or in combination with one another and with other spinal implant components in spinal stabilization and reconstruction procedures.

14 Claims, 10 Drawing Sheets

SPINAL STABILIZATION AND RECONSTRUCTION WITH FUSION RODS

BACKGROUND

Normal intervertebral discs between endplates of adjacent vertebrae distribute forces between the vertebrae and cushion vertebral bodies. The spinal discs and/or vertebral bodies along the spinal column may be displaced or damaged due to trauma, disease or aging. As a result, stabilization systems may be implanted along the spinal column to distribute loading from the spinal column between intact spinal structures. Such systems have employed rods positioned along two or more vertebrae and secured to the pedicles of the vertebrae with screws or hooks.

In the sacral region, rigid stabilization and reconstruction systems have been employed that include elongate members with a rod portion extending along the lumbar vertebrae and a plate portion secured to the sacral vertebrae or to the ilium. In view of the spinal column loading being supported by the rigid construct, such systems can also employ a separate fusion construct between the iliac wings to fuse the sacral region. Other stabilization systems and techniques along other portions of the spinal column also can involve implants in the disc space in combination with rods or plates extending along the vertebrae. The mass and various numerous separate components in such procedures can increase the potential for complications associated with such procedures, both during surgery and post-operatively.

SUMMARY

The present invention is directed to spinal fusion rods and systems and methods for employing the same in spinal stabilization and reconstructions procedures. The spinal fusion rods can include a rod portion and a fusion portion extending from the rod portion along a longitudinal axis. The fusion portion can be formed by a cannulated, fenestrated body along the fusion rod. The fusion rods can be employed alone or in combination with other fusion rods in the stabilization and reconstruction systems. The rod portion can be attached to one or more vertebrae along the spinal column with the fusion portion engaging the ilium, sacrum or other pelvic structure. In other procedures, the rod portion is engaged to the pelvic region and the fusion portion engages an endplate of a vertebral body. Other systems are contemplated where the rod portion is engaged along one or more vertebrae and the fusion portion engages a vertebral endplate.

In one aspect, a fusion rod comprises a rod portion extending at least partially along a longitudinal axis from a first end to an intermediate portion. The fusion rod also includes a fusion portion extending at least partially along the longitudinal axis from the intermediate portion to a second end opposite the first end. The fusion portion includes a body defining a cavity and a number of wall openings about the body in communication with the cavity.

In another aspect, a fusion rod comprises an elongated solid rod portion extending along a longitudinal axis and a mesh cage-like structure extending from an end of the rod portion along the longitudinal axis.

In a further aspect, a spinal stabilization and reconstruction system comprise first and second fusion rods each including a rod portion extending along a longitudinal axis and a fusion portion extending from the rod portion along the longitudinal axis. Each of the fusion portions includes a cavity and a plurality of wall openings in communication with the cavity. The system further includes a plurality of anchors to secure the rod portions to at least one vertebra.

In still another aspect, a surgical method comprises: securing a rod portion of a fusion rod along a side of at least one lumbar vertebra; positioning a mesh portion of the fusion rod that extends from an end of the rod portion of the fusion rod in contact with a pelvic structure; and supporting spinal loads with the rod portion and the mesh structure while allowing bone growth into the mesh structure.

In yet another aspect, a surgical method comprises: securing a rod portion of a fusion rod with a pelvic structure; and positioning a fusion portion of the fusion rod in contact with an endplate of a lumbar vertebra. The fusion portion and the rod portion are engaged with one another along a central longitudinal axis.

These and other aspects are further discussed below.

DETAILED DESCRIPTION OF THE ILLUSTRATED EMBODIMENTS

For the purposes of promoting an understanding of the principles of the present invention, reference will now be made to the embodiments illustrated in the drawings, and specific language will be used to describe the same. It will nevertheless be understood that no limitation of the scope of the invention is intended thereby. Any alterations and further modification in the described processes, systems, or devices, and any further applications of the principles of the invention as described herein are contemplated as would normally occur to one skilled in the art to which the invention relates.

Spinal reconstruction and stabilization systems can be employed to reconstruct and stabilize portions of the spinal column, including the sacral region, to provide support of spinal column loads when spinal structures are no longer capable or effective to do so. The stabilization and reconstruction systems can include fusion rods having a rod portion and a fusion portion. The rod portion can be secured along portions of the spinal column or pelvic regions where due to anatomical constraints smaller or lower profile implants are desired. The fusion portion can be located along or adjacent to portions of the spinal column or pelvic region where fusion of adjacent bony structures to the fusion rod or to another is desired. The reconstruction systems can employ anchors to secure the fusion rod to bony tissue, and cross-connectors and other stabilization members to secure adjacent fusion rods to one another in side-by-side relation and also to adjacent bony structures. The reconstruction systems can employ fasteners to secure the rod portion and the fusion portion to the adjacent pelvic structure or vertebral bodies.

Figure 1A:
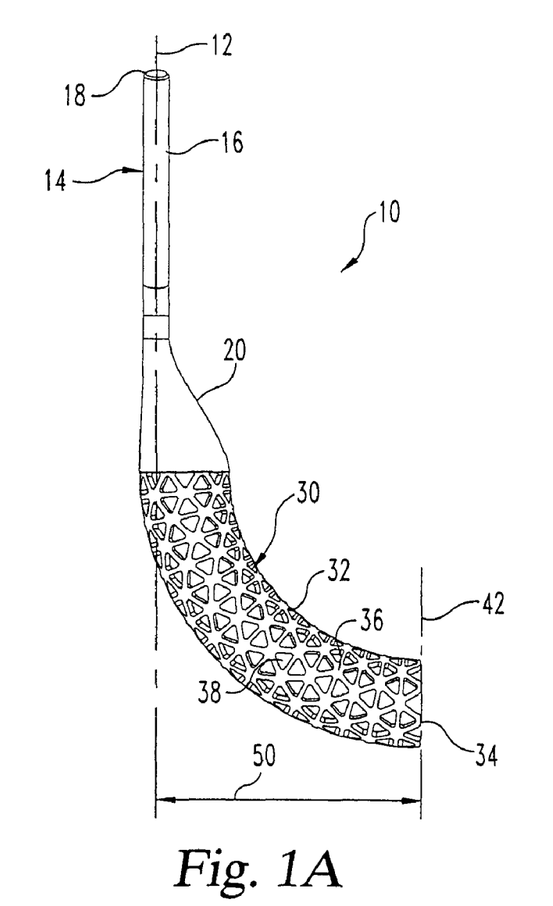
FIG. 1A is an elevation view of a fusion rod according to one embodiment.
Figure 1B:
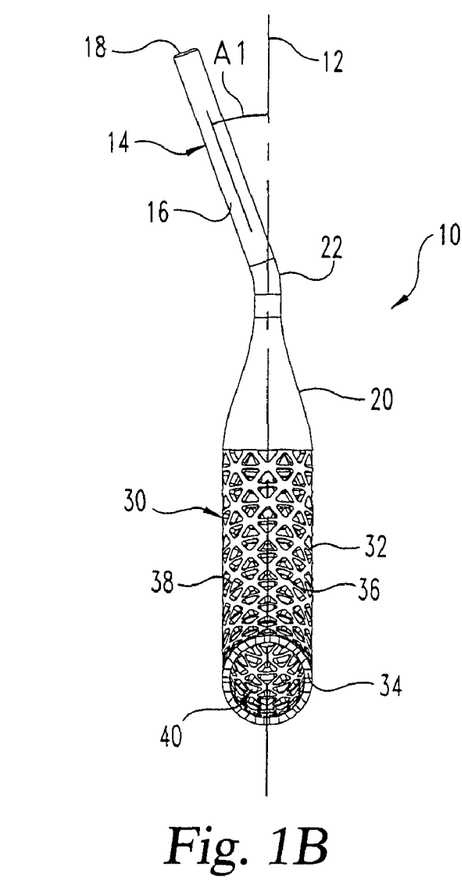
FIG. 1B is an elevation view of the fusion rod of FIG. 1A rotated 90 degrees about its central longitudinal axis.

In FIGS. 1A and 1B, there is shown a fusion rod 10 extending along a longitudinal axis 12. Fusion rod 10 includes a rod portion 14 and a fusion portion 30. Rod portion 14 includes an elongated cylindrical body 16 extending along longitudinal axis 12 from a first end 18 to an intermediate portion 20. Rod portion 14 can include a cylindrical shape with a circular cross-section orthogonally to longitudinal axis 12. Other embodiments contemplate other cross-sectional shapes for rod portion 14, including oval, square, rectangular, polygonal, and non-circular shapes. The shapes can also vary along the length. Rod portion 14 can be solid as shown. Other embodiments contemplate rod portion 14 with a central lumen to receive a guidewire or for passage of bone cement or growth material. Rod portion 14 can include one or more holes, pits, recesses, apertures or other openings extending therethrough or therein transversely to longitudinal axis 12.

As shown in FIG. 1B, rod portion 14 can extend in a plane including longitudinal axis 12, and can be angled relative to longitudinal axis 12 in that plane at an angle A1. Angle A1 can be formed by a bend 22 adjacent intermediate portion 20. Angle A1 can range from 0 degrees to 90 degrees. In one form, angle A1 ranges from 0 degrees to 45 degrees to conform rod portion 14 to extend along the spinal column. Angle A1 can be adjustable by the surgeon or attendant bending rod portion 14 relative to longitudinal axis 12 in any plane extending through longitudinal axis 12 to provide the desired fit with the anatomy.

Fusion portion 30 includes a body 32 extending from intermediate portion 20 to a second end 34. Body 32 can include a cross-section that is larger than that of rod portion 14. Body 32 can provide a mesh cage-like structure along fusion rod 10. Intermediate portion 20 can provide a gradual, tapering transition between the cross-sections. Intermediate portion 20 can be integrally formed with or joined to rod portion 14 and fusion portion 30. Other embodiments contemplate one or both of rod portion 14 and fusion portion 30 are removably joined with intermediate portion 20. Intermediate portion 20 can include a solid body to provide strength to the connection between rod portion 14 and fusion portion 30. Other embodiments contemplate intermediate portion 20 includes holes, cannulations, recesses, pits, apertures, or other structures.

Fusion portion 30 includes body 32 that is cannulated to define a lumen or cavity 40 extending from second end 34 to intermediate portion 20. Body 32 also includes a wall 36 extending around cavity 40 that includes a number of fenestrations or openings 38 extending through wall 36 and that are in communication with cavity 40. The openings 38 can form a mesh-like structure for wall 36 that provides strong load carrying capabilities with an open cell form to facilitate bone growth and incorporation of the fusion portion 30 with bony tissue. The openings can be triangular in shape as shown, or include any other shape, such as circular, oval, diamond, polygonal, non-circular, and random shapes. In addition, the opening shapes can be different from one another in the same fusion portion 30.

Body 32 can lie along longitudinal axis 12 in one plane as shown in FIG. 1B and be curved to extend from the plane that includes longitudinal axis 12 and angled rod portion 14, as shown in FIG. 1A. In the illustrated embodiment, rod portion 14 is angled in a plane that is orthogonal to the plane in which fusion portion 30 is curved. The curved fusion body can extend to end 34 lying in a plane 42 that is parallel to the plane including longitudinal axis 12 and the angled rod portion 14. The orientation of end 34 can provide a better fit with certain portions of the patient's spinal anatomy, such as those portions that are oriented to extend generally along the central axis of the spinal column.

Figure 2A:
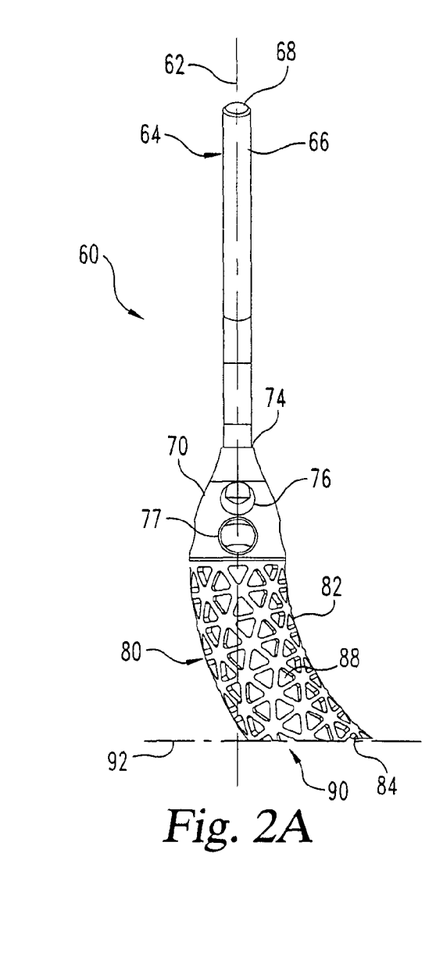
FIG. 2A is an elevation view of a fusion rod according to another embodiment.
Figure 2B:
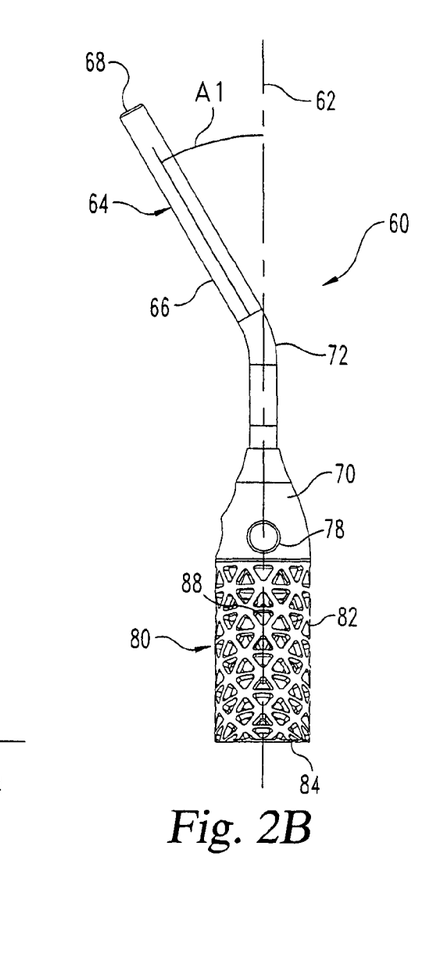
FIG. 2B is an elevation view of the fusion rod of FIG. 2A rotated 90 degrees about its central longitudinal axis.
Figure 2C:
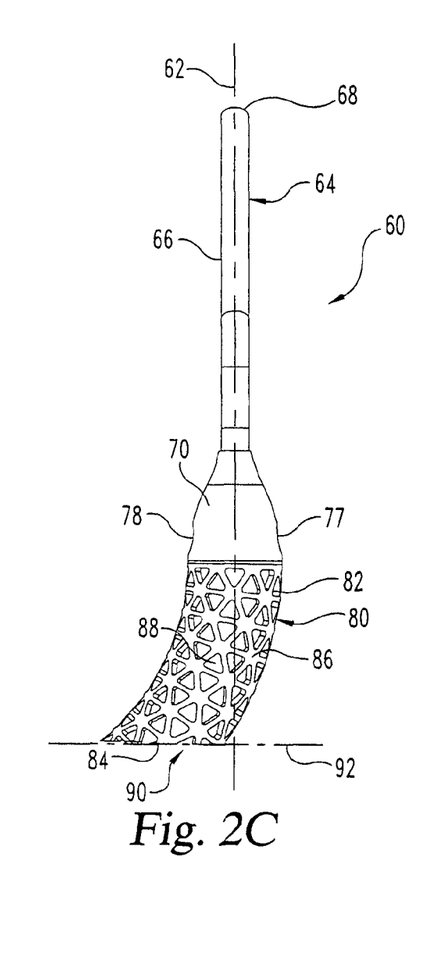
FIG. 2C is an elevation view of the fusion rod of FIG. 2A rotated 180 degrees about its central longitudinal axis.

In FIGS. 2A-2C, there is shown a fusion rod 60 extending along a longitudinal axis 62. Fusion rod 60 includes a rod portion 64 and a fusion portion 80. Rod portion 64 includes an elongated cylindrical body 66 extending along longitudinal axis 62 from a first end 68 to an intermediate portion 70. Rod portion 64 can include a cylindrical shape with a circular cross-section orthogonally to longitudinal axis 62. Other embodiments contemplate other cross-sectional shapes for rod portion 64, including oval, square, rectangular, polygonal, and non-circular shapes. The cross-sections can be uniform or varying along the length of rod portion 64. Rod portion 64 can be solid as shown. Other embodiments contemplate rod portion 64 with a central lumen to receive a guidewire or for passage of bone cement or growth material. Rod portion 64 can include one or more holes, apertures, pits, recesses, or other openings extending therethrough or therein transversely to longitudinal axis 62.

As shown in FIGS. 2B-2C, rod portion 64 can extend in a plane including longitudinal axis 62, and can be angled relative to or bent to be angled relative to longitudinal axis 62 in that plane at an angle A1 as discussed above with respect to rod portion 14 of fusion rod 10. Angle A1 can be formed by a bend 72 adjacent intermediate portion 70.

Fusion portion 80 includes a body 82 extending from intermediate portion 70 to a second end 84. Body 82 can include a cross-section that is larger than that of rod portion 64. Body 82 can provide a mesh cage-like structure along fusion rod 60. Intermediate portion 70 can provide a gradual, tapering transition between the cross-sections. Intermediate portion 70 can be integrally formed with or joined to rod portion 64 and fusion portion 80. In the illustrated embodiment, intermediate portion 70 includes an axially oriented end opening 74 and rod portion 64 is positioned therein. Intermediate portion 70 includes a hole 76 in a side thereof to receive an engaging member such as a set screw or other fastener to couple rod portion 64 in intermediate portion 70.

The separability of rod portion 64 and fusion portion 80 allows the surgeon to select from rod portions and fusions portions of differing lengths, cross-sections, materials, or other properties to secure to one another based on the anatomical conditions or other treatment options that may be desired. In one embodiment, fusion portion 80 can be formed of resorbable material that resorbs over time to provide short-term stabilization, and rod portion 64 can be non-resorbable to provide long-term stabilization. In another embodiment, rod portion 64 can be formed of resorbable material that resorbs over time to provide short-term stabilization, and fusion portion 80 can be non-resorbable to provide long-term stabilization. In another embodiment, both the rod portion and the fusion portion are resorbable. In yet another embodiment, both the rod portion and the fusion portion are non-resorbable. Rod portion 64 can be made from a first material and fusion portion 80 can be made from a second material that differs from the first material. For example, rod portion 64 could be made from a metal or metal alloy such as titanium or stainless steel, and fusion portion 80 could be made from a polymer or poly-ether type material such as polyetheretherketone (PEEK). In another example, fusion portion 80 could be made from a metal or metal alloy such as titanium or stainless steel, and rod portion 64 could be made from a polymer or poly-ether type material such as PEEK.

As discussed further below, intermediate portion 70 includes receptacles 77, 78 to receive other components of a stabilization system. It should be understood, however, that fusion rod 60 can include an intermediate portion like that discussed above for fusion rod 10, and fusion rod 10 can include an intermediate portion like that discussed with respect to fusion rod 60.

Fusion portion 80 includes body 82 that is cannulated to define a lumen or cavity 90 extending from second end 84 to intermediate portion 70. Body 82 also includes a wall 86 extending around cavity 90 that includes a number of fenestrations or openings 88 extending through wall 86 and that are in communication with cavity 90. The openings can be of any shape and form a mesh-like structure for wall 86 that provides strong load carrying capabilities with an open cell form to facilitate bone growth and incorporation of the fusion portion 80 with bony tissue.

Body 82 can lie along longitudinal axis 62 in one plane as shown in FIG. 2B and be curved to extend away from the plane that includes longitudinal axis 62 and angled rod portion 64, as shown in FIGS. 2A and 2C. The curved fusion body 82 can extend to end 84 lying in a plane 92 that is orthogonal to longitudinal axis 12. The orientation of end 84 can provide a better fit with the patient's anatomy in certain locations, such as when positioned against vertebral endplates, or in any orientation that generally parallels the coronal plane.

Figure 3A:
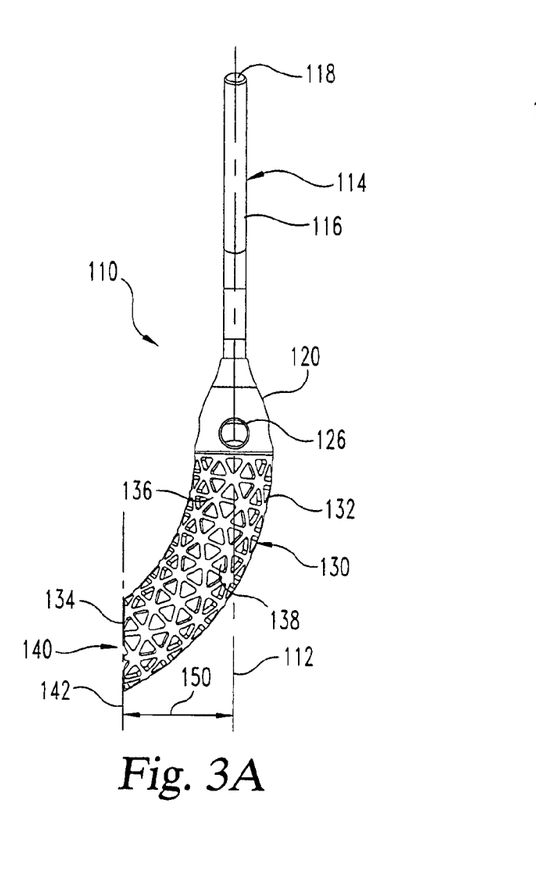
FIG. 3A is an elevation view of a fusion rod according to another embodiment.
Figure 3B:
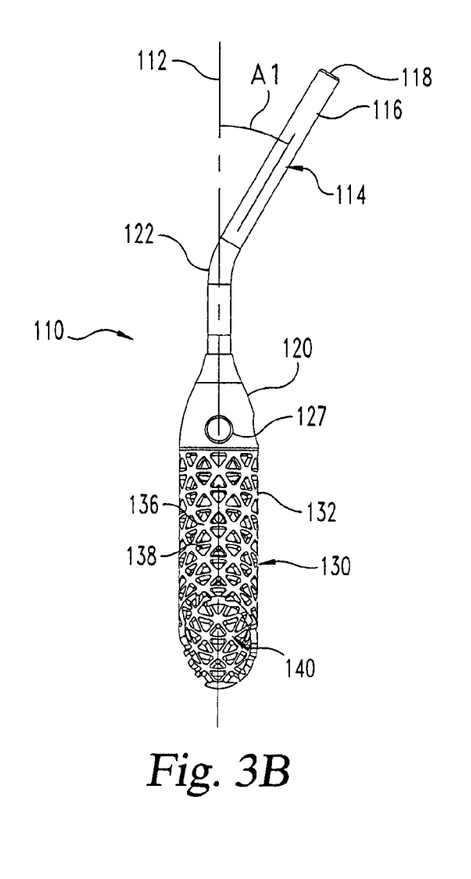
FIG. 3B is an elevation view of the fusion rod of FIG. 3A rotated 90 degrees about its central longitudinal axis.
Figure 3C:
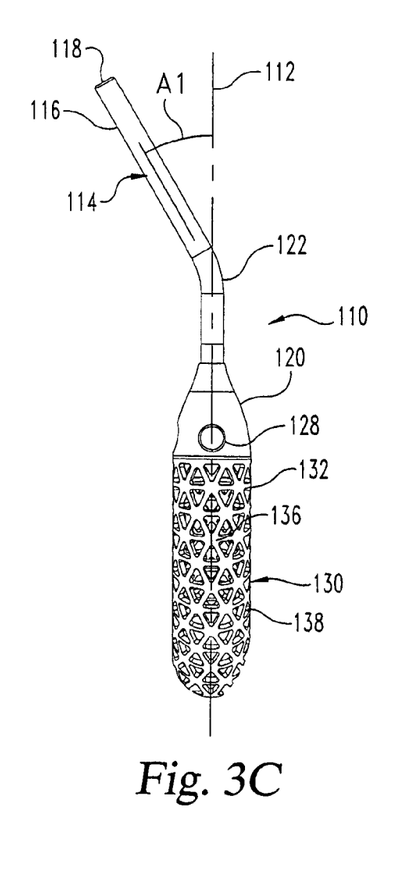
FIG. 3C is an elevation view of the fusion rod of FIG. 3A rotated 180 degrees about its central longitudinal axis.

In FIGS. 3A-3C, there is shown a fusion rod 110 extending along a longitudinal axis 112. Fusion rod 110 includes a rod portion 114 and a fusion portion 130. Rod portion 114 includes an elongated cylindrical body 116 extending along longitudinal axis 112 from a first end 118 to an intermediate portion 120. Rod portion 114 can include a cylindrical shape with a circular cross-section orthogonally to longitudinal axis 112. Other embodiments contemplate other cross-sectional shapes for rod portion 114, including oval, square, rectangular, polygonal, and non-circular shapes. The cross-section can be the same or variable along the length of rod portion 114. Rod portion 114 can be solid as shown. Other embodiments contemplate rod portion 114 with a central lumen to receive a guidewire or for passage of bone cement or growth material. Rod portion 114 can include one or more holes, apertures, pits, recesses or other openings extending therethrough or therein transversely to longitudinal axis 112.

As shown in FIG. 3A, rod portion 114 can extend in a plane including longitudinal axis 112, and can be angled relative to or bent to be angled relative to longitudinal axis 112 in that plane at an angle A1 as discussed above with respect to rod portion 14 of fusion rod 10. Angle A1 can be formed by a bend 122 adjacent intermediate portion 120.

Fusion portion 130 includes a body 132 extending from intermediate portion 120 to a second end 134. Body 132 can provide a mesh cage-like structure along fusion rod 110. Body 132 can include a cross-section that is larger than that of rod portion 114. Intermediate portion 120 can provide a gradual, tapering transition between the cross-sections. Intermediate portion 120 can be integrally formed with or joined to rod portion 114 and fusion portion 130. Intermediate portion 120 includes axially aligned receptacles 126, 127, 128 in respective sides thereof. An engaging member such as a set screw or other fastener can be positioned in one receptacle 126 while another component of the system extends through or into receptacles 127, 128. The engaging member in receptacle 126 can secure the transverse component to intermediate portion 120. It should be understood, however, that fusion rod 110 can include an intermediate portion like that discussed above for fusion rods 10 and 60, and fusion rods 10 and 60 can include an intermediate portion like that discussed with respect to fusion rod 110.

Fusion portion 130 includes body 132 that is cannulated to define a lumen or cavity 140 extending from second end 134 to intermediate portion 120. Body 132 also includes a wall 136 extending around cavity 140 that includes a number of fenestrations or openings 138 extending through wall 136 and that are in communication with cavity 140. The openings can be of any shape and form a mesh-like structure for wall 136 that provides strong load carrying capabilities with an open cell form to facilitate bone growth and incorporation of the fusion portion 130 with bony tissue.

Body 132 can lie along longitudinal axis 112 in one plane as shown in FIGS. 3B, 3C and be curved to extend away from the plane that includes longitudinal axis 112 and angled rod portion 114, as shown in FIG. 3A. In the illustrated embodiment, rod portion 114 is angled in a plane that is orthogonal to the plane in which fusion portion 130 is curved. The curved fusion body 132 can extend to end 134 lying in a plane 142 that is parallel to longitudinal axis 12, similar to fusion rod 10 discussed above. However, distance 150 between plane 142 and longitudinal axis 112 is substantially less than distance 50 between plane 42 and longitudinal axis 12 to provide a different anatomical fit. Stated another way, the length of the arc long which body 132 extends is less than the length of the arc along which body 32 extends. The orientation of end 134 can provide a better fit with the patient's anatomy in certain locations, such as when positioned against anatomical structures that extend along the central axis of the spinal column.

Figure 4A:
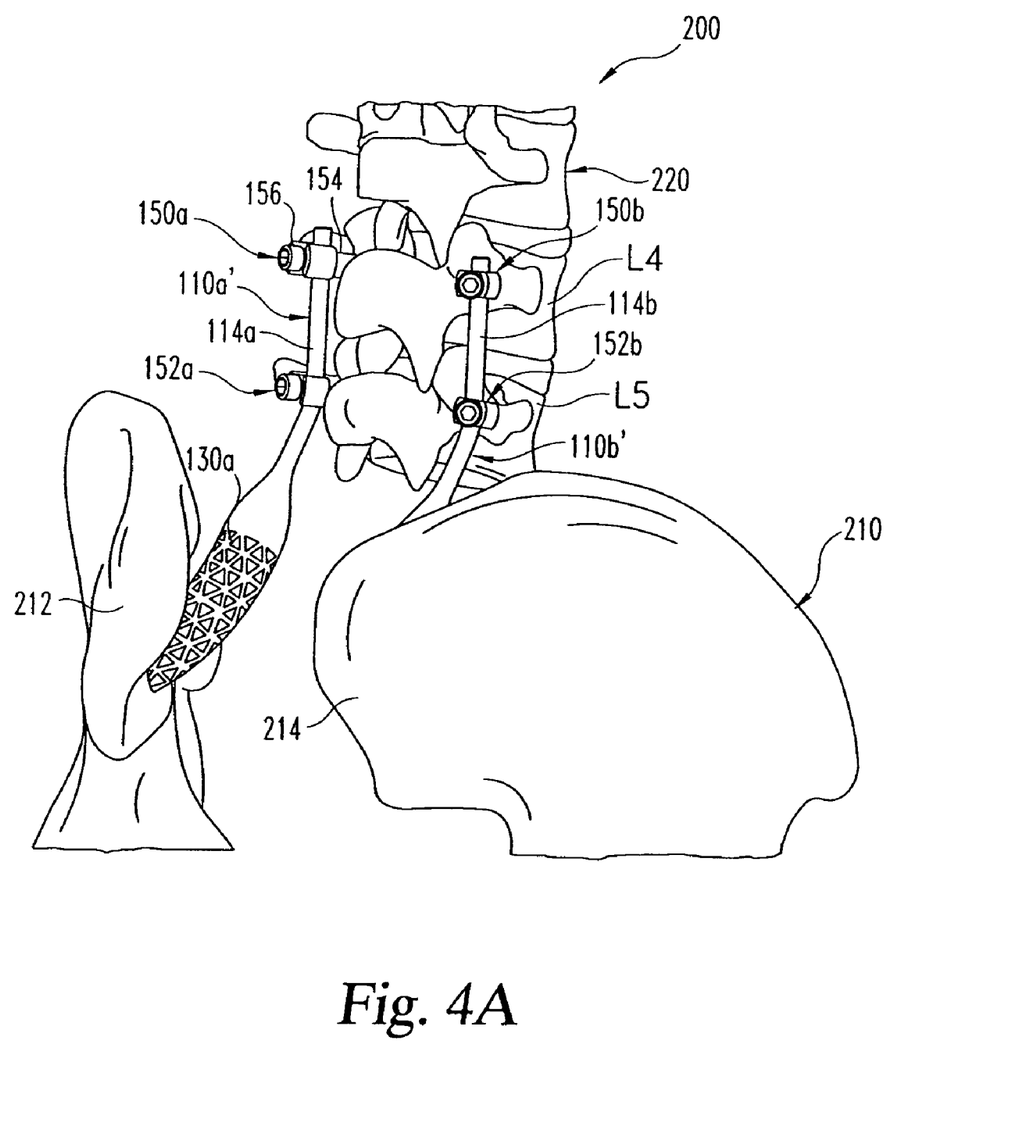
FIG. 4A is a perspective view looking anteriorly from a posterior side of the spinal column at one embodiment spinal stabilization and reconstruction system secured to the spinal column and pelvic region.
Figure 4B:
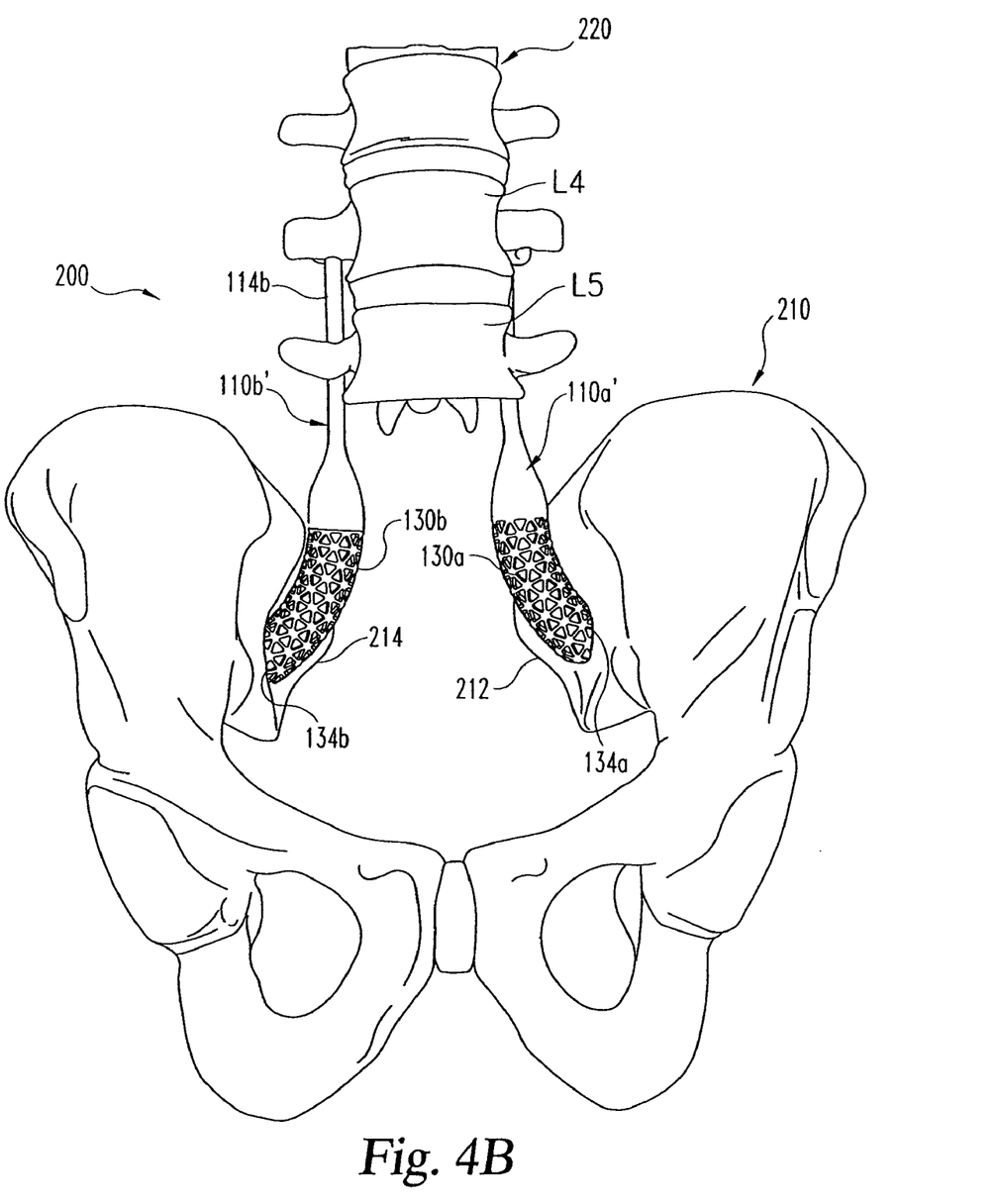
FIG. 4B is another perspective view of the spinal stabilization and reconstruction system of FIG. 4A looking posteriorly from an anterior side of the spinal column.

Referring now to FIGS. 4A and 4B, there is shown an example of a spinal reconstruction and stabilization system 200 employing fusion rod 110', which is similar to fusion rod 110 but includes an integral rod portion and intermediate portion with no receptacles in the intermediate portion, although such is not precluded. Reconstruction system 200 includes first fusion rod 110a' along one side of the spinal column 220 and a second fusion rod 110b' along the other side of spinal column 220. Fusions rods 110a', 110b' extend along the central axis of the spinal column and extradiscally between the vertebrae L4 and L5. Bone anchors 150a, 150b in the respective pedicles of vertebra L4 and bone anchors 152a, 152b in the respective pedicles of vertebra L5 are in the form of pedicle screws. Rod portion 114a is positioned between anchors 150a, 152a and rod portion 114b is positioned between anchors 150b, 152b.

In the illustrated embodiment, anchors 150, 152 can be identical and each can include a proximal U-shaped head 154 and a distal screw-like bone engaging portion to engage bony tissue of the vertebral body. The head can receive the rod portion therein, and an engaging member 156 in the form of a set screw as shown, or in the form of a cap or the like, can be engaged to the head to capture the rod portion therein. Other embodiments contemplate that the anchors are different from one another. Other forms for the anchors include hooks, staples, cables, wires, plates, intradiscal implants, and other spinal implant devices. The head portion can be pivotally coupled to the screw portion to provide a multi-axial or multi-positional arrangement therebetween so that the head can be re-oriented as desired. The head portion can also be fixed relative to the screw portion to provide a fixed, uni-axial arrangement therebetween.

With the respective rod portions 114a, 114b secured to vertebrae L4 and L5, fusion portion 130a, 130b extends caudally therefrom where ends 134a, 134b contact the respective ilium 212, 214 of the pelvic structure 210. The ends 134a, 134b distribute the spinal column loading over the respective ilium. Fusion portions 130a, 130b can include bone growth material packed or positioned therein to support bone growth for further mechanical stabilization of the reconstructed portion of the spine. Containment of the graft and bone growth material in the mesh structure of fusion portions 130a, 130b may increase the rate of the osteogenic process. To provide additional stability, the fusion portions 130a, 130b can be fastened or secured to the pelvic structure with one or more wires, sutures, cables, bone screws, staples, rods, connectors, or other securing device. The fasteners can extend through one or more of the wall openings of the mesh structure and engage the adjacent bony structure to secure the mesh portion thereto.

Figure 5:
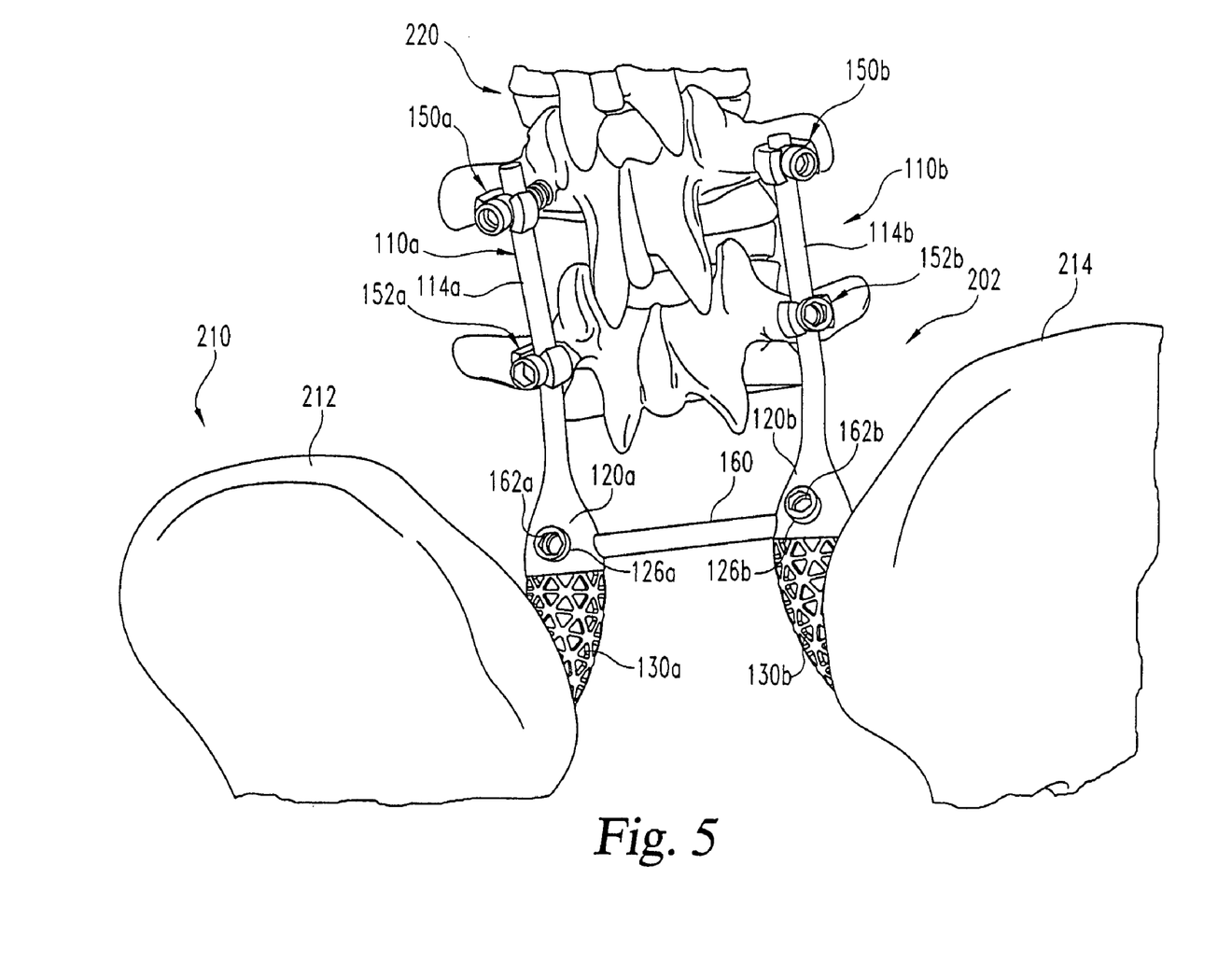
FIG. 5 is a perspective view looking anteriorly from a posterior side of the spinal column at another embodiment spinal stabilization and reconstruction system secured to the spinal column and pelvic region.

Referring to FIG. 5, there is shown the spinal column 220 with another embodiment reconstruction and stabilization system 202. Reconstruction system 202 includes fusion rods 110a, 110b with rod portions 114a, 114b secured to vertebrae L4, L5 and fusion portions 130a, 130b secured to ilia 212, 214 in the manner discussed above with respect to fusion rods 110a', 110b'. However, system 202 includes a transverse stabilization member 160 extending between intermediate portions 120a, 120b and positioned in the receptacles therein. An engaging member 162a, 162b, in the form of a set screw is positioned in the respective receptacle 126a, 126b to secure the respective adjacent end of transverse stabilization member 160 therein.

Figure 6:
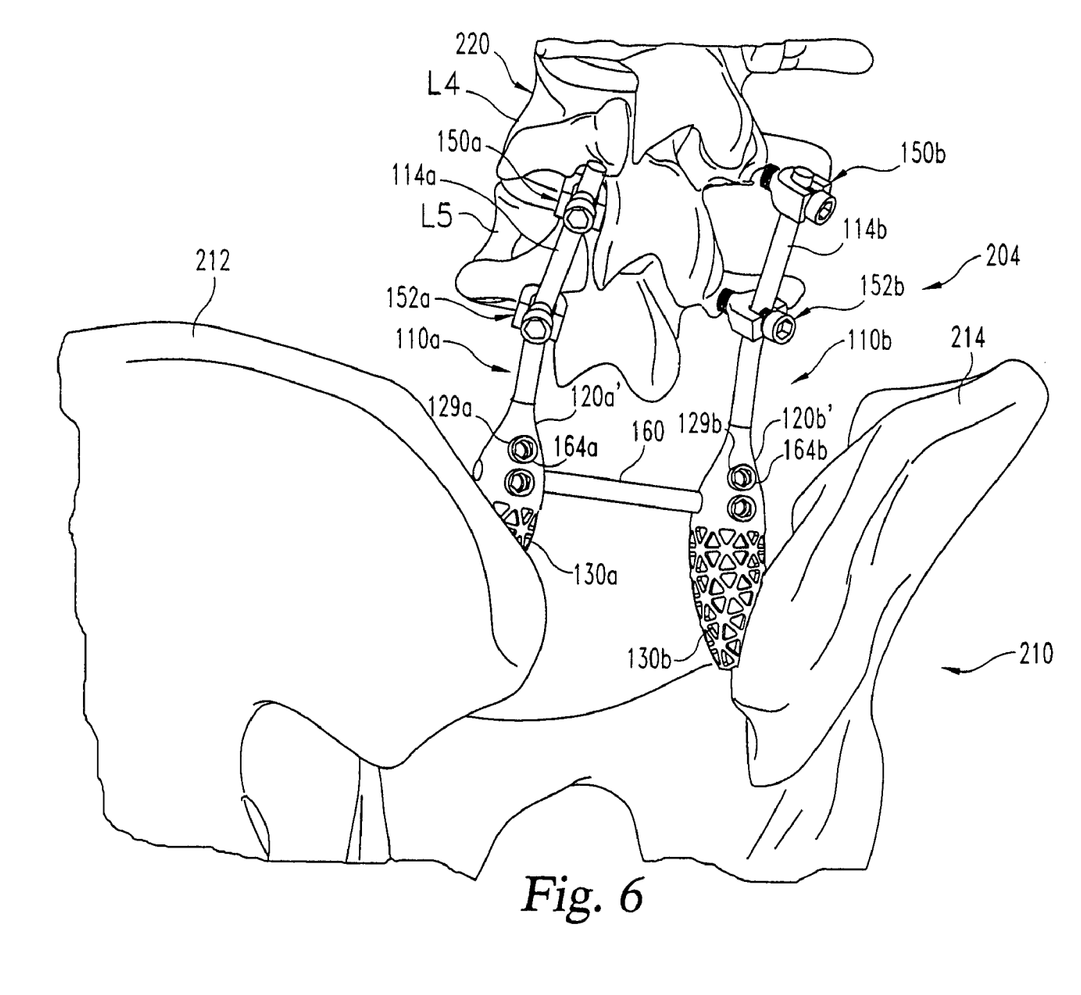
FIG. 6 is a perspective view looking anteriorly from a posterior side of the spinal column at another embodiment spinal stabilization and reconstruction system secured to the spinal column and pelvic region.

In FIG. 6 there is shown a reconstruction and stabilization system 204 that is similar to reconstruction system 202 discussed above with respect to FIG. 5. However, reconstruction system 204 includes fusions rods 110a, 110b with the rod portions 114a, 114b removably coupled to the respective intermediate portions 120a', 120b'. The intermediate portions 120a', 120b' are provided with a fourth receptacle 129a, 129b, respectively, to receive a second engaging member 164a, 164b to secure the removable rod portion 114a, 114b in the respective intermediate portion 120a', 120b'.

Figure 7:
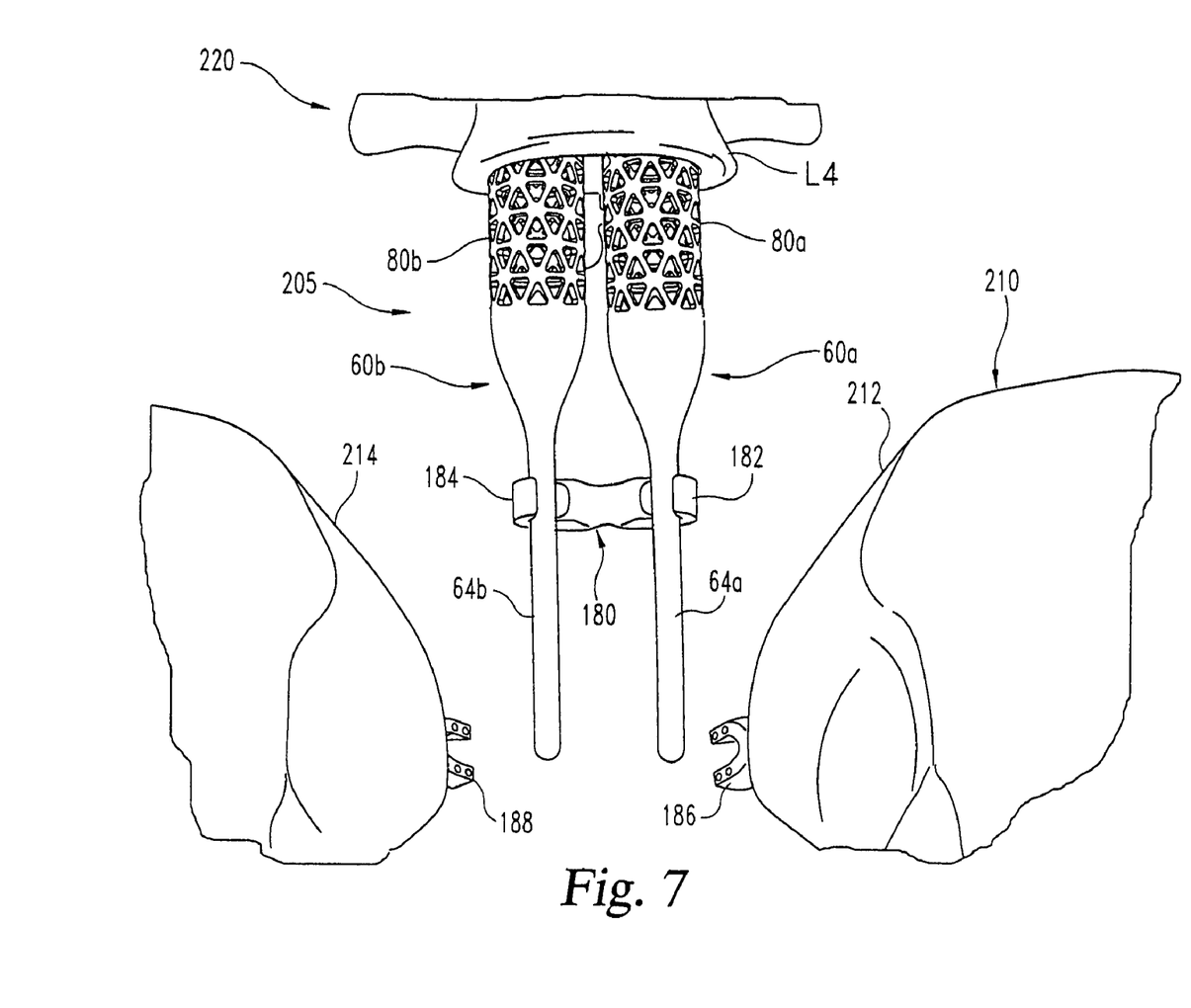
FIG. 7 is a perspective view of another embodiment spinal stabilization and reconstruction system looking posteriorly from an anterior side of the spinal column.

Referring to FIG. 7 there is shown a reconstruction system 205 that includes first and second fusions rods 60a, 60b. Fusion rods 60a, 60b include fusion portions 80a, 80b, respectively, that have ends positioned in contact with the endplate of the L4 vertebra. Contact with endplates of other lumbar vertebrae is also contemplated. Fusion portions 80a, 80b extend from the endplate toward the pelvic structure 210. Rod portions 64a, 64b extend from the fusion portions 80a, 80b in a side-by-side relation to one another. Rod portions 64a, 64b can be secured to one another with a transverse cross-link member 180 extending therebetween. Cross-link member 180 can include end hooks 182, 184 that extend around the respective rod portion and maintain the spacing between rod portions 64a, 64b and providing additional stability to the construct. The ends of rod portions 64a, 64b can be linked with a rod or other structure and engaged to the ilia 212, 214 with respective ones of the iliac screws 186, 188.

Figure 8:
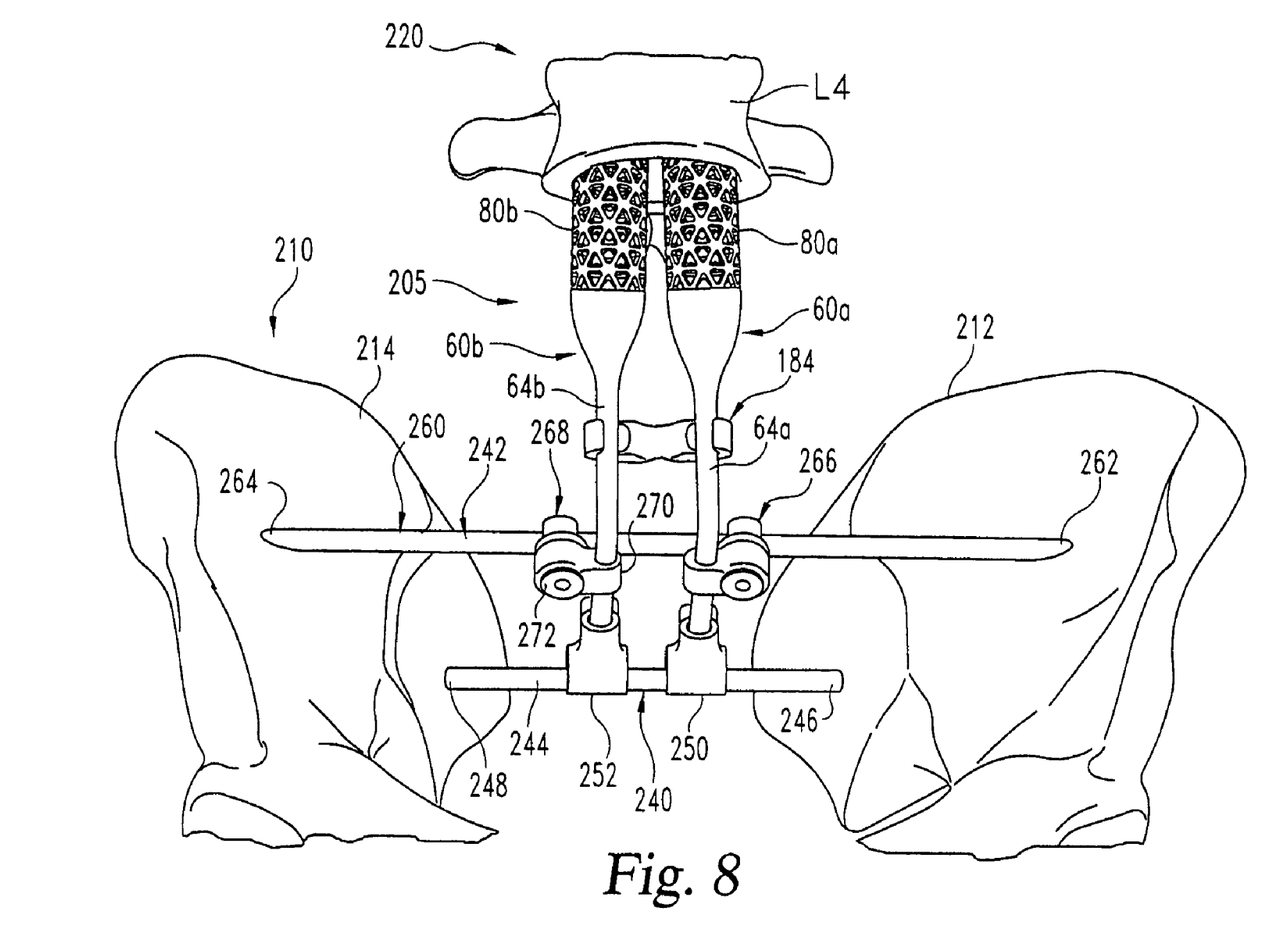
FIG. 8 is a perspective view of another embodiment spinal stabilization and reconstruction system looking posteriorly from an anterior side of the spinal column.

Referring to FIG. 8, there is shown another embodiment reconstruction and stabilization system 206 that is similar to reconstruction system 205 but there is shown a pair of transverse stabilization members 240, 242 secured to the rod portions 64a, 64b in addition to the pelvic structure. Transverse stabilization member 240 includes an elongated rod-like body 244 that extends between opposite ends 246, 248 contacting the ilia 212, 214, respectively. Body 244 extends through T-shaped coupling members 250, 252 engaged to the ends of the respective rod portions 64a, 64b. The coupling members 250, 252 can be secured to the rod portions 64a, 64b with an engaging member such as a set screw, or formed as an integral part of the rod portion. Ends 246, 248 can be embedded into the pelvic structure or engaged thereto with screws or some other fastener or fastening system.

Transverse stabilization member 242 includes an elongated rod-like body 260 that extends between opposite ends 262, 264 contacting the ilia 212, 214, respectively. Body 260 extends through clamping assemblies 266, 268 engaged along the respective rod portions 64a, 64b between the ends of rod portions 64a, 64b and the bend forming the angular offset of rod portions 64a, 64b. Cross-link 184 is located between the fusion portions 80a, 80b and the respective bends forming the angular offset portion of the rod portions 64a, 64b.

The clamping assemblies 266, 268 can be identical to one another. Clamping assemblies 266, 268 include a C-shaped clamp member 270 positioned around the rod portion 64a, 64b and an eye-bolt 272 extending through an end of the clamp member 270 and defining a passage for receiving the transverse stabilization member 242 therethrough. When the eye-bolt is tightened, the C-shaped clamp member 270 clamps in position around the respective rod portion 64a, 64b and the transverse stabilization member 242 is clamped in the eyebolt passage.

Figure 9:
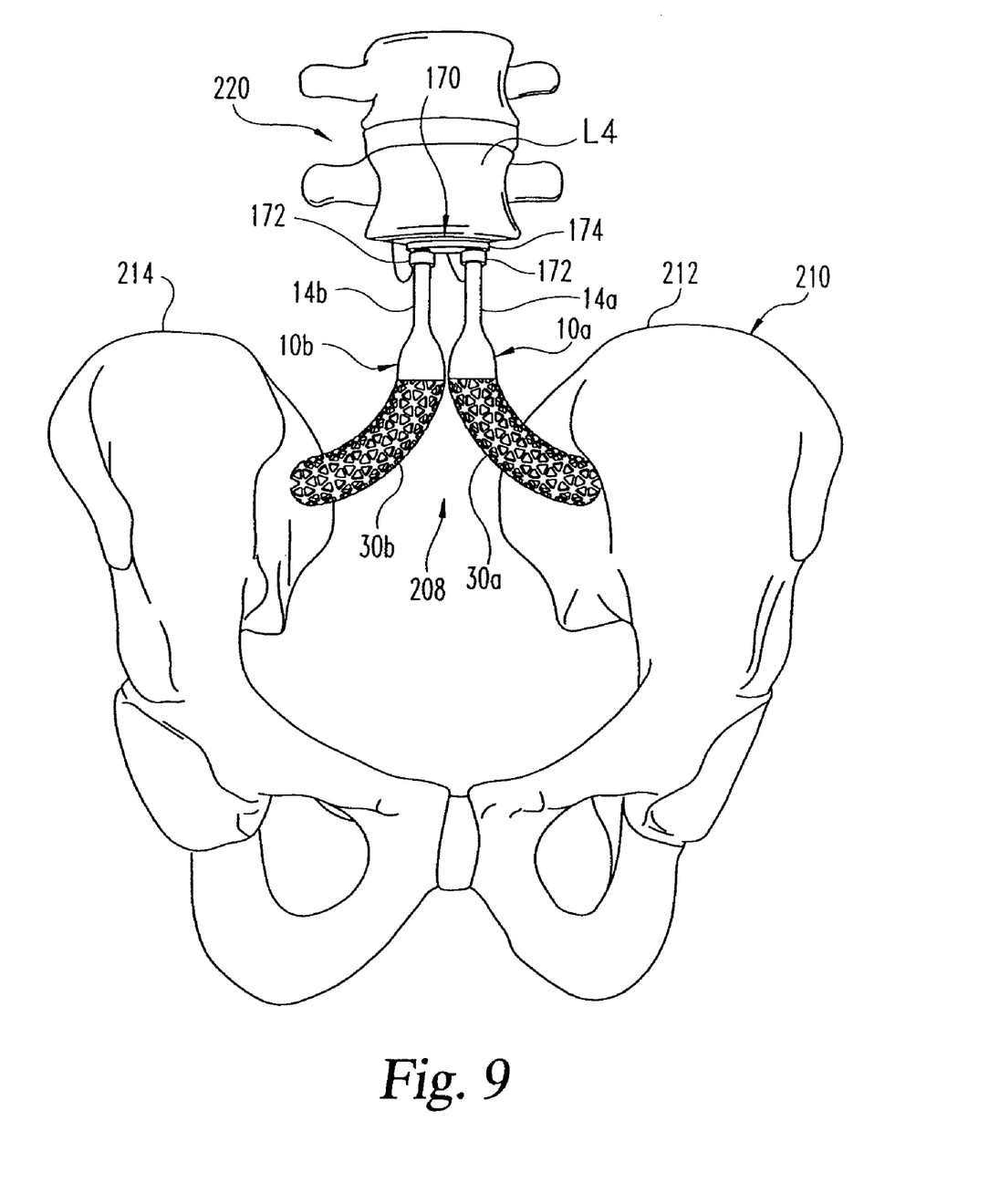
FIG. 9 is a perspective view of another embodiment spinal stabilization and reconstruction system looking posteriorly from an anterior side of the spinal column.

Referring to FIG. 9, there is shown reconstruction system 208 that includes fusion rods 10a, 10b positioned alongside one another. Fusion portions 30a, 30b are located with their respective second ends in contact with the respective adjacent ilia 212, 214. Fusion portions 30a, 30b are oriented so the rod portions 14a, 14b extend toward the endplate of the L4 vertebra, although contact with an endplate of other lumbar vertebrae is also contemplated. An end member 170 can be provided with clamps 172 that secure the ends of rod portions 14a, 14b. End member 170 also includes an end portion 174 contacts the endplate to distribute the supporting load over the end plate while the fusions rods 10a, 10b are linked to one another.

The stabilization and reconstruction systems are shown in regard to sacral and lumbar vertebrae reconstruction systems. Such systems can be employed in other regions of the spine, and can also be employed with single fusion rods or with three or more fusion rods.

While the invention has been illustrated and described in detail in the drawings and the foregoing description, the same is considered to be illustrative and not restrictive in character. All changes and modifications that come within the spirit of the invention are desired to be protected.

What is claimed is:

1. A fusion rod, comprising:
a rod portion extending at least partially along and lying on a longitudinal axis from a first end to an intermediate portion wherein said intermediate portion is located on said longitudinal axis;
a fusion portion extending at least partially along the longitudinal axis from said intermediate portion to a second end opposite said first end, said fusion portion including a body defining a cavity for bone growth material, wherein said cavity extends from said longitudinal axis to said second end and said fusion portion includes a number of wall openings about said body in communication with said cavity, wherein said number of wall openings define a mesh cage-like structure on at least a portion of said fusion portion that is located on the longitudinal axis, wherein:
said fusion portion is curved in a direction along said longitudinal axis so that a center of said fusion portion defines a first between said intermediate portion and said second end, wherein said longitudinal axis lies in said first plane;
said second end of said fusion portion defines an opening into said cavity that lies in a second plane that is parallel to said longitudinal axis and orthogonal to said first plane; and
when viewed in a direction looking along said first plane and toward said second end of said fusion portion, said rod portion includes a bend forming an angled rod portion that extends at an angle with said longitudinal axis from said bend to said first end of said rod portion so that said first end of said rod portion is offset from said longitudinal axis with said angled rod portion and said longitudinal axis defining third plane that is orthogonal to said first plane and parallel to said second plane.

2. The fusion rod of claim 1, further comprising bone graft in said cavity.

3. The fusion rod of claim 1, wherein said rod portion is removably engageable with said intermediate portion.

4. The fusion rod of claim 3, wherein said intermediate portion includes a hole extending therein and further comprising an engaging member in said hole to secure said rod portion to said intermediate portion.

5. The fusion rod of claim 1, wherein said intermediate portion includes a cross-section orthogonally to said longitudinal axis, said cross-section tapering from said fusion portion to said rod portion.

6. The fusion rod of claim 1, wherein said rod portion is complete solid and forms an elongated cylinder along said longitudinal axis.

7. The fusion rod of claim 1, wherein said mesh cage-like structure extends circumferentially about at least a portion of said fusion portion.

8. The fusion rod of claim 1, wherein said mesh cage-like structure includes a cross-sectional size that is substantially greater than a cross-sectional size of said rod portion.

9. The fusion rod of claim 1, wherein said mesh cage-like structure includes a wall extending about said central cavity, said wall defining a number of openings in communication with said central cavity.

10. A fusion rod, comprising:
an elongated solid rod portion extending along and lying on a longitudinal axis and a mesh cage-like structure extending from an end of said rod portion located on said longitudinal axis, wherein said mesh cage-like structure defines a central cavity for bone growth material and said central cavity is located on said longitudinal axis and said mesh cage-like structure extends around said central cavity from said longitudinal axis to a second end of said mesh cage-like structure opposite said rod portion that is offset from said longitudinal axis, wherein:
said mesh cage-like structure is curved in a direction along said longitudinal axis between end of said rod portion and said second end so that a center of said mesh cage-like structure defines a first plane between said rod portion and said second end wherein said longitudinal axis lies in said first plane;
said second end of said mesh cage-like structure defines an opening into said cavity that lies in a second plane that is parallel to said longitudinal axis and orthogonal to said first plane; and
when viewed in a direction looking along said first plane and toward said second end of said mesh cage-like structure, said rod portion includes a bend forming an angled rod portion that extends at an angle with said longitudinal axis from said bend to an outer end of said rod portion so that said outer end of said rod portion is offset from said longitudinal axis with said angled rod portion and said longitudinal axis defining a third plane that is orthogonal to said first plane and parallel to said second plane.

11. The fusion rod of claim 10, further comprising an intermediate portion extending between and transitioning in cross-section between said mesh cage-like structure and said rod portion.

12. The fusion rod of claim 11, wherein said mesh cage-like structure includes a cross-sectional size that is substantially greater than a cross-sectional size of said rod portion.

13. The fusion rod of claim 10, wherein said mesh cage-like structure includes a wall extending about said central cavity, said wall defining a number of openings in communication with said central cavity.

14. The fusion rod of claim 10, wherein said rod portion forms a completely solid cylinder along a substantial portion of its length.

* * * * *